United States Patent
Neculescu et al.

(10) Patent No.: US 7,335,273 B2
(45) Date of Patent: Feb. 26, 2008

(54) METHOD OF MAKING STRAND-REINFORCED ELASTOMERIC COMPOSITES

(75) Inventors: Cristian M. Neculescu, Neenah, WI (US); Peiguang Zhou, Appleton, WI (US); Daniel J. Wideman, Menasha, WI (US); Bruce Achter, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 367 days.

(21) Appl. No.: 10/330,042

(22) Filed: Dec. 26, 2002

(65) Prior Publication Data
US 2004/0123938 A1 Jul. 1, 2004

(51) Int. Cl.
*A61F 13/15* (2006.01)
*B32B 37/00* (2006.01)

(52) U.S. Cl. .............. 156/229; 156/161; 156/163; 156/164; 156/244.11

(58) Field of Classification Search .......... 156/229, 156/160–165, 77, 78, 246, 244.11; 604/385.2; 428/212, 215, 219
See application file for complete search history.

(56) References Cited

U.S. PATENT DOCUMENTS

| 3,338,992 | A | 8/1967 | Kinney |
| 3,341,394 | A | 9/1967 | Kinney |
| 3,502,538 | A | 3/1970 | Petersen |
| 3,502,763 | A | 3/1970 | Hartmann |
| 3,542,615 | A | 11/1970 | Dobo et al. |
| 3,692,618 | A | 9/1972 | Dorschner et al. |
| 3,802,817 | A | 4/1974 | Matsuki et al. |
| 3,904,465 | A | 9/1975 | Haase et al. |
| 3,949,128 | A | 4/1976 | Ostermeier |
| 3,973,063 | A | 8/1976 | Clayton |
| 4,090,385 | A | 5/1978 | Packard |
| 4,107,364 | A | 8/1978 | Sisson |
| 4,135,037 | A | 1/1979 | Udipi et al. |
| 4,148,676 | A | 4/1979 | Paquette et al. |
| 4,209,563 | A | 6/1980 | Sisson |
| 4,211,807 | A | 7/1980 | Yazawa et al. |
| 4,239,578 | A | 12/1980 | Gore |
| 4,241,123 | A | 12/1980 | Shih |
| 4,248,652 | A | 2/1981 | Civardi et al. |
| 4,259,220 | A * | 3/1981 | Bunnelle et al. .............. 525/98 |
| 4,285,998 | A | 8/1981 | Thibodeau |
| 4,300,562 | A | 11/1981 | Pieniak |
| 4,302,495 | A | 11/1981 | Marra |
| 4,303,571 | A | 12/1981 | Jansen et al. |

(Continued)

FOREIGN PATENT DOCUMENTS

CA 2165486 6/1996

(Continued)

*Primary Examiner*—Jeff H Aftergut
(74) *Attorney, Agent, or Firm*—Pauley Peterson & Erickson

(57) ABSTRACT

A method of making mutually-reinforced elastic strand/film composites and laminates in which film breakage, strand breakage, and strand alignment problems are minimized or avoided. The method includes casting an elastomeric adhesive film onto a chill roll, extruding elastic strands onto the film while the film is on a chill roll, and stretching the film and strand composite. The stretched composite may be laminated between two facing sheets. Additionally, tension in the composite may be controlled through film composition, strand composition, add-on rate, stretching the composite, and combinations of any of these approaches.

22 Claims, 9 Drawing Sheets

U.S. PATENT DOCUMENTS

| | | |
|---|---|---|
| 4,304,234 A | 12/1981 | Hartmann |
| 4,310,594 A | 1/1982 | Yamazaki et al. |
| 4,319,572 A | 3/1982 | Widlund et al. |
| 4,323,534 A | 4/1982 | DesMarais |
| 4,333,782 A | 6/1982 | Pieniak |
| 4,340,558 A | 7/1982 | Hendrickson |
| 4,340,563 A | 7/1982 | Appel et al. |
| 4,375,446 A | 3/1983 | Fujii et al. |
| 4,402,688 A | 9/1983 | Julemont |
| 4,405,397 A | 9/1983 | Teed |
| 4,413,623 A | 11/1983 | Pieniak |
| 4,417,935 A | 11/1983 | Spencer |
| 4,418,123 A * | 11/1983 | Bunnelle et al. ............ 428/517 |
| 4,438,167 A | 3/1984 | Schwarz |
| 4,440,819 A | 4/1984 | Rosser et al. |
| 4,490,427 A | 12/1984 | Grant et al. |
| 4,496,417 A | 1/1985 | Haake et al. |
| 4,500,316 A | 2/1985 | Damico |
| 4,507,163 A | 3/1985 | Menard |
| 4,522,863 A | 6/1985 | Keck et al. |
| 4,525,407 A | 6/1985 | Ness |
| 4,543,099 A | 9/1985 | Bunnelle et al. |
| 4,548,859 A | 10/1985 | Kline et al. |
| 4,552,795 A | 11/1985 | Hansen et al. |
| 4,555,811 A | 12/1985 | Shimalla |
| 4,556,596 A * | 12/1985 | Meuli ......................... 428/152 |
| 4,572,752 A | 2/1986 | Jensen et al. |
| 4,586,199 A | 5/1986 | Birring |
| D284,036 S | 6/1986 | Birring |
| 4,606,964 A | 8/1986 | Wideman |
| 4,618,384 A | 10/1986 | Sabee |
| 4,626,305 A | 12/1986 | Suzuki et al. |
| 4,636,419 A | 1/1987 | Madsen et al. |
| 4,640,859 A | 2/1987 | Hansen et al. |
| 4,644,045 A | 2/1987 | Fowells |
| 4,652,487 A | 3/1987 | Morman |
| 4,656,081 A | 4/1987 | Ando et al. |
| 4,657,793 A | 4/1987 | Fisher |
| 4,657,802 A | 4/1987 | Morman |
| 4,661,389 A | 4/1987 | Mudge et al. |
| 4,663,220 A | 5/1987 | Wisneski et al. |
| 4,666,543 A | 5/1987 | Kawano |
| 4,675,068 A | 6/1987 | Lundmark |
| 4,683,877 A | 8/1987 | Ersfeld et al. |
| 4,687,477 A | 8/1987 | Suzuki et al. |
| 4,692,368 A | 9/1987 | Taylor et al. |
| 4,692,371 A | 9/1987 | Morman et al. |
| 4,698,242 A | 10/1987 | Salerno |
| 4,704,116 A | 11/1987 | Enloe |
| 4,718,901 A | 1/1988 | Singheimer |
| 4,719,261 A | 1/1988 | Bunnelle et al. |
| 4,720,415 A | 1/1988 | Vander Wielen et al. |
| 4,725,468 A | 2/1988 | McIntyre |
| 4,726,874 A | 2/1988 | VanVliet |
| 4,734,311 A | 3/1988 | Sokolowski |
| 4,734,320 A | 3/1988 | Ohira et al. |
| 4,734,447 A | 3/1988 | Hattori et al. |
| 4,735,673 A | 4/1988 | Piron |
| 4,756,942 A | 7/1988 | Aichele |
| 4,761,198 A | 8/1988 | Salerno |
| 4,762,582 A | 8/1988 | de Jonckheere |
| 4,775,579 A | 10/1988 | Hagy et al. |
| 4,777,080 A | 10/1988 | Harris, Jr. et al. |
| 4,789,699 A | 12/1988 | Kieffer et al. |
| 4,798,603 A | 1/1989 | Meyer et al. |
| 4,801,345 A | 1/1989 | Dussaud et al. |
| 4,801,482 A | 1/1989 | Goggans et al. |
| 4,803,117 A | 2/1989 | Daponte |
| 4,804,577 A | 2/1989 | Hazelton et al. |
| 4,813,946 A * | 3/1989 | Sabee .................... 604/385.27 |
| 4,818,597 A | 4/1989 | DaPonte et al. |
| 4,826,415 A | 5/1989 | Mende |
| 4,837,715 A | 6/1989 | Ungpiyakul et al. |
| 4,842,666 A | 6/1989 | Werenicz |
| 4,854,985 A | 8/1989 | Soderlund et al. |
| 4,854,989 A | 8/1989 | Singheimer |
| 4,863,779 A | 9/1989 | Daponte |
| 4,867,735 A | 9/1989 | Wogelius |
| 4,874,447 A | 10/1989 | Hazelton et al. |
| 4,883,482 A | 11/1989 | Gandrez et al. |
| 4,883,549 A | 11/1989 | Frost et al. |
| 4,891,258 A | 1/1990 | Fahrenkrug |
| 4,892,536 A | 1/1990 | DesMarais et al. |
| 4,892,903 A | 1/1990 | Himes |
| 4,900,619 A | 2/1990 | Ostrowski et al. |
| 4,906,507 A | 3/1990 | Grynaeus et al. |
| 4,908,247 A | 3/1990 | Baird et al. |
| 4,908,253 A | 3/1990 | Rasmussen |
| 4,910,064 A | 3/1990 | Sabee |
| 4,917,696 A | 4/1990 | De Jonckheere |
| 4,917,746 A | 4/1990 | Kons et al. |
| 4,929,492 A | 5/1990 | Carey, Jr. et al. |
| 4,935,021 A | 6/1990 | Huffman et al. |
| 4,938,757 A | 7/1990 | Van Gompel et al. |
| 4,938,821 A | 7/1990 | Soderlund et al. |
| 4,939,016 A * | 7/1990 | Radwanski et al. ......... 428/152 |
| 4,940,464 A | 7/1990 | Vam Gompel et al. |
| 4,965,122 A | 10/1990 | Morman |
| 4,968,313 A | 11/1990 | Sabee |
| 4,970,259 A | 11/1990 | Mitchell et al. |
| 4,977,011 A | 12/1990 | Smith |
| 4,984,584 A | 1/1991 | Hansen et al. |
| 4,994,508 A | 2/1991 | Shiraki et al. |
| 4,995,928 A | 2/1991 | Sabee |
| 4,998,929 A | 3/1991 | Bjorksund et al. |
| 5,000,806 A | 3/1991 | Merkatoris et al. |
| 5,002,815 A | 3/1991 | Yamanaka et al. |
| 5,005,215 A | 4/1991 | McIlquham |
| 5,013,785 A | 5/1991 | Mizui |
| 5,028,646 A | 7/1991 | Miller et al. |
| 5,032,120 A * | 7/1991 | Freeland et al. ....... 604/385.27 |
| 5,034,008 A | 7/1991 | Breitkopf |
| 5,045,133 A | 9/1991 | DaPonte et al. |
| 5,046,272 A | 9/1991 | Vogt et al. |
| 5,060,349 A | 10/1991 | Walton et al. |
| 5,073,436 A | 12/1991 | Antonacci et al. |
| 5,093,422 A | 3/1992 | Himes |
| 5,100,435 A | 3/1992 | Onwumere |
| 5,104,116 A | 4/1992 | Pohjola |
| 5,108,820 A | 4/1992 | Kaneko et al. |
| 5,112,889 A | 5/1992 | Miller et al. |
| 5,114,087 A | 5/1992 | Fisher et al. |
| 5,114,781 A | 5/1992 | Morman |
| 5,116,662 A | 5/1992 | Morman |
| 5,147,487 A | 9/1992 | Nomura et al. |
| 5,149,741 A | 9/1992 | Alper et al. |
| 5,163,932 A | 11/1992 | Nomura et al. |
| D331,627 S | 12/1992 | Igaue et al. |
| 5,169,706 A | 12/1992 | Collier, IV et al. |
| 5,169,712 A | 12/1992 | Tapp |
| 5,176,668 A | 1/1993 | Bernardin |
| 5,176,672 A | 1/1993 | Bruemmer et al. |
| 5,186,779 A | 2/1993 | Tubbs |
| 5,192,606 A | 3/1993 | Proxmire et al. |
| 5,198,281 A | 3/1993 | Muzzy et al. |
| 5,200,246 A | 4/1993 | Sabee |
| 5,204,429 A | 4/1993 | Kaminsky et al. |
| D335,707 S | 5/1993 | Igaue et al. |
| 5,209,801 A | 5/1993 | Smith |
| 5,219,633 A | 6/1993 | Sabee |
| 5,224,405 A | 7/1993 | Pohjola |
| 5,226,992 A | 7/1993 | Morman |
| 5,229,191 A | 7/1993 | Austin |
| 5,232,777 A | 8/1993 | Sipinen et al. |

| | | | | | | |
|---|---|---|---|---|---|---|
| 5,236,430 A | 8/1993 | Bridges | | 5,540,796 A | 7/1996 | Fries |
| 5,236,770 A | 8/1993 | Assent et al. | | 5,540,976 A | 7/1996 | Shawver et al. |
| 5,238,733 A | 8/1993 | Joseph et al. | | 5,543,206 A | 8/1996 | Austin et al. |
| 5,246,433 A | 9/1993 | Hasse et al. | | 5,545,158 A | 8/1996 | Jessup |
| D340,283 S | 10/1993 | Igaue et al. | | 5,545,285 A | 8/1996 | Johnson |
| 5,252,170 A | 10/1993 | Schaupp | | 5,549,964 A | 8/1996 | Shohji et al. |
| 5,259,902 A | 11/1993 | Muckenfuhs | | 5,560,792 A * | 10/1996 | Anthony ..................... 152/415 |
| 5,260,126 A | 11/1993 | Collier, IV et al. | | 5,569,232 A | 10/1996 | Roe et al. |
| 5,272,236 A | 12/1993 | Lai et al. | | 5,575,783 A | 11/1996 | Clear et al. |
| 5,278,272 A | 1/1994 | Lai et al. | | 5,576,090 A | 11/1996 | Suzuki |
| 5,288,791 A | 2/1994 | Collier, IV et al. | | 5,582,668 A | 12/1996 | Kling |
| 5,290,842 A | 3/1994 | Sasaki et al. | | 5,591,152 A | 1/1997 | Buell et al. |
| 5,296,080 A | 3/1994 | Merkatoris et al. | | 5,591,792 A | 1/1997 | Hattori et al. |
| 5,304,599 A | 4/1994 | Himes | | 5,595,618 A | 1/1997 | Fries et al. |
| 5,308,345 A | 5/1994 | Herrin | | 5,597,430 A | 1/1997 | Rasche |
| 5,312,500 A | 5/1994 | Kurihara et al. | | 5,612,118 A | 3/1997 | Schleinz et al. |
| 5,324,580 A | 6/1994 | Allan et al. | | 5,614,276 A | 3/1997 | Petsetakis |
| 5,332,613 A | 7/1994 | Taylor et al. | | 5,620,780 A | 4/1997 | Krueger et al. |
| 5,334,437 A | 8/1994 | Zafiroglu | | 5,624,740 A | 4/1997 | Nakata |
| 5,334,446 A | 8/1994 | Quantrille et al. | | 5,626,573 A | 5/1997 | Igaue et al. |
| 5,336,545 A | 8/1994 | Morman | | 5,628,856 A | 5/1997 | Dobrin et al. |
| 5,336,552 A | 8/1994 | Strack et al. | | 5,645,672 A | 7/1997 | Dobrin |
| 5,342,341 A | 8/1994 | Igaue et al. | | 5,652,041 A | 7/1997 | Buerger et al. |
| 5,342,469 A | 8/1994 | Bodford et al. | | 5,660,664 A | 8/1997 | Herrmann |
| 5,360,854 A | 11/1994 | Bozich, Jr. | | 5,663,228 A | 9/1997 | Sasaki et al. |
| 5,364,382 A | 11/1994 | Latimer et al. | | 5,669,897 A | 9/1997 | Lavon et al. |
| 5,366,793 A | 11/1994 | Fitts, Jr. et al. | | 5,674,216 A | 10/1997 | Buell et al. |
| 5,376,198 A | 12/1994 | Fahrenkrug et al. | | 5,680,653 A | 10/1997 | Mathis et al. |
| 5,376,430 A | 12/1994 | Swenson et al. | | 5,681,302 A | 10/1997 | Melbye et al. |
| 5,382,400 A | 1/1995 | Pike et al. | | 5,683,787 A | 11/1997 | Boich et al. |
| 5,385,775 A | 1/1995 | Wright | | 5,690,626 A | 11/1997 | Suzuki et al. |
| 5,389,168 A * | 2/1995 | Litchholt et al. .............. 156/77 | | 5,691,034 A | 11/1997 | Krueger et al. |
| 5,389,173 A | 2/1995 | Merkatoris et al. | | 5,693,038 A | 12/1997 | Suzuki et al. |
| 5,389,438 A | 2/1995 | Miller et al. | | 5,695,849 A | 12/1997 | Shawver et al. |
| 5,393,599 A | 2/1995 | Quantrille et al. | | 5,702,378 A | 12/1997 | Widlund et al. |
| 5,399,219 A | 3/1995 | Roessler et al. | | 5,707,709 A | 1/1998 | Blake |
| 5,405,682 A | 4/1995 | Shawver et al. | | 5,720,838 A | 2/1998 | Nakata |
| 5,407,507 A | 4/1995 | Ball | | 5,733,635 A | 3/1998 | Terakawa et al. |
| 5,411,618 A | 5/1995 | Jocewicz, Jr. | | 5,733,822 A | 3/1998 | Gessner et al. |
| 5,413,654 A | 5/1995 | Igaue et al. | | 5,735,839 A | 4/1998 | Kawaguchi et al. |
| 5,413,849 A | 5/1995 | Austin et al. | | 5,736,219 A | 4/1998 | Suehr et al. |
| 5,415,644 A | 5/1995 | Enloe | | 5,746,731 A | 5/1998 | Hisada |
| 5,415,649 A | 5/1995 | Watanabe et al. | | 5,749,865 A | 5/1998 | Yamamoto et al. |
| 5,415,925 A | 5/1995 | Austin et al. | | 5,749,866 A | 5/1998 | Roe et al. |
| 5,422,172 A | 6/1995 | Wu | | 5,766,389 A | 6/1998 | Brandon et al. |
| 5,425,987 A | 6/1995 | Shawver et al. | | 5,766,737 A | 6/1998 | Willey et al. |
| 5,429,629 A | 7/1995 | Latimer et al. | | 5,769,838 A | 6/1998 | Buell et al. |
| 5,429,694 A | 7/1995 | Herrmann | | 5,769,993 A | 6/1998 | Baldauf |
| 5,431,644 A | 7/1995 | Sipinen et al. | | 5,772,649 A | 6/1998 | Siudzinski |
| 5,431,991 A | 7/1995 | Quantrille et al. | | 5,773,373 A | 6/1998 | Wynne et al. |
| 5,447,462 A | 9/1995 | Smith et al. | | 5,773,374 A | 6/1998 | Wood et al. |
| 5,447,508 A | 9/1995 | Numano et al. | | 5,788,804 A | 8/1998 | Horsting |
| 5,449,353 A | 9/1995 | Watanabe et al. | | 5,789,065 A | 8/1998 | Haffner et al. |
| 5,464,401 A | 11/1995 | Hasse et al. | | 5,789,328 A | 8/1998 | Kurihara et al. |
| 5,472,775 A | 12/1995 | Obijeski et al. | | 5,789,474 A | 8/1998 | Lu et al. |
| 5,476,458 A | 12/1995 | Glaug et al. | | 5,800,903 A | 9/1998 | Wood et al. |
| 5,476,563 A | 12/1995 | Nakata | | 5,804,021 A | 9/1998 | Abuto et al. |
| 5,484,645 A | 1/1996 | Lickfield et al. | | 5,804,286 A | 9/1998 | Quantrille et al. |
| 5,486,166 A | 1/1996 | Bishop et al. | | 5,814,176 A | 9/1998 | Proulx |
| 5,490,846 A | 2/1996 | Ellis et al. | | 5,817,087 A | 10/1998 | Takabayashi et al. |
| 5,496,298 A | 3/1996 | Kuepper et al. | | 5,818,719 A | 10/1998 | Brandon et al. |
| 5,498,468 A | 3/1996 | Blaney | | 5,830,203 A | 11/1998 | Suzuki et al. |
| 5,500,075 A | 3/1996 | Herrmann | | 5,834,089 A | 11/1998 | Jones et al. |
| 5,501,679 A | 3/1996 | Krueger et al. | | 5,836,931 A | 11/1998 | Toyoda et al. |
| 5,503,919 A * | 4/1996 | Litchholt et al. ........... 428/101 | | 5,836,932 A | 11/1998 | Buell et al. |
| 5,509,915 A | 4/1996 | Hanson et al. | | 5,840,412 A | 11/1998 | Wood et al. |
| 5,514,470 A | 5/1996 | Haffner et al. | | 5,840,633 A | 11/1998 | Kurihara et al. |
| 5,516,476 A | 5/1996 | Haggard et al. | | 5,846,232 A | 12/1998 | Serbiak et al. |
| 5,523,146 A | 6/1996 | Bodford et al. | | 5,849,001 A | 12/1998 | Torimae et al. |
| 5,527,300 A | 6/1996 | Sauer | | 5,856,387 A | 1/1999 | Sasaki et al. |
| 5,531,850 A | 7/1996 | Herrmann | | 5,860,945 A | 1/1999 | Cramer et al. |
| 5,534,330 A | 7/1996 | Groshens | | 5,865,933 A | 2/1999 | Morin et al. |
| 5,536,563 A | 7/1996 | Shah et al. | | 5,876,392 A | 3/1999 | Hisada |

| | | | | | |
|---|---|---|---|---|---|
| 5,879,776 A | 3/1999 | Nakata | 2002/0164465 A1 | 11/2002 | Curro et al. |
| 5,882,573 A | 3/1999 | Kwok et al. | | | |
| 5,885,656 A | 3/1999 | Goldwasser | FOREIGN PATENT DOCUMENTS | | |
| 5,885,686 A | 3/1999 | Cederblad et al. | | | |
| 5,897,546 A | 4/1999 | Kido et al. | DE | 34 23 644 | 1/1986 |
| 5,899,895 A | 5/1999 | Robles et al. | DE | 37 34 963 | 4/1988 |
| 5,902,540 A | 5/1999 | Kwok | EP | 0 155 636 | 9/1985 |
| 5,904,298 A | 5/1999 | Kwok et al. | EP | 0 172 037 | 2/1986 |
| 5,916,206 A | 6/1999 | Otsubo et al. | EP | 0 217 032 | 4/1987 |
| 5,921,973 A | 7/1999 | Newkirk et al. | EP | 0 239 080 | 9/1987 |
| 5,930,139 A | 7/1999 | Chapdelaine et al. | EP | 0 330 716 A2 | 9/1989 |
| 5,931,581 A | 8/1999 | Garberg et al. | EP | 0 380 781 | 8/1990 |
| 5,932,039 A | 8/1999 | Popp et al. | EP | 0 396 800 | 11/1990 |
| 5,941,865 A | 8/1999 | Otsubo et al. | EP | 414 917 | 3/1991 |
| D414,262 S | 9/1999 | Ashton et al. | EP | 0 456 885 | 11/1991 |
| 5,952,252 A | 9/1999 | Shawver et al. | EP | 0 547 497 | 6/1993 |
| 5,964,970 A | 10/1999 | Woolwine et al. | EP | 0 582 569 | 2/1994 |
| 5,964,973 A | 10/1999 | Heath et al. | EP | 0 604 731 | 7/1994 |
| 5,990,377 A | 11/1999 | Chen et al. | EP | 0 617 939 | 10/1994 |
| 5,993,433 A | 11/1999 | St. Louis et al. | EP | 676 438 | 10/1995 |
| 5,997,521 A | 12/1999 | Robles et al. | EP | 0 688 550 | 12/1995 |
| 6,004,306 A | 12/1999 | Robles et al. | EP | 0 689 815 | 1/1996 |
| 6,009,558 A | 1/2000 | Rosch et al. | EP | 0 713 546 | 5/1996 |
| 6,033,502 A | 3/2000 | Coenen et al. | EP | 0 743 052 | 11/1996 |
| 6,045,543 A | 4/2000 | Pozniak et al. | EP | 0 753 292 | 1/1997 |
| 6,048,326 A | 4/2000 | Davis et al. | EP | 0 761 193 | 3/1997 |
| 6,057,024 A | 5/2000 | Mleziva et al. | EP | 0 761 194 | 3/1997 |
| 6,066,369 A | 5/2000 | Schulz et al. | EP | 0 763 353 | 3/1997 |
| 6,087,550 A | 7/2000 | Anderson-Fischer et al. | EP | 0 787 474 | 8/1997 |
| 6,090,234 A | 7/2000 | Barone et al. | EP | 0 802 251 A1 | 10/1997 |
| 6,092,002 A | 7/2000 | Kastman et al. | EP | 0 803 602 A1 | 10/1997 |
| 6,093,663 A | 7/2000 | Ouellette et al. | EP | 0 806 196 | 11/1997 |
| 6,096,668 A | 8/2000 | Abuto et al. | EP | 0 814 189 | 12/1997 |
| 6,123,694 A | 9/2000 | Pieniak et al. | EP | 0 873 738 | 10/1998 |
| 6,132,410 A | 10/2000 | Van Gompel et al. | EP | 0 888 101 | 1/1999 |
| 6,149,637 A * | 11/2000 | Allen et al. ............. 604/366 | EP | 0 901 780 | 3/1999 |
| 6,152,904 A | 11/2000 | Matthews et al. | EP | 1 013 251 | 6/2000 |
| 6,159,584 A * | 12/2000 | Eaton et al. ............. 428/198 | EP | 1 164 007 | 12/2001 |
| 6,169,848 B1 | 1/2001 | Henry | EP | 1 321 288 A2 | 6/2003 |
| 6,183,587 B1 | 2/2001 | McFall et al. | GB | 2 244 422 | 12/1991 |
| 6,183,847 B1 | 2/2001 | Goldwasser | GB | 2 250 921 | 6/1992 |
| 6,197,845 B1 | 3/2001 | Janssen et al. | GB | 2 253 131 | 9/1992 |
| 6,214,476 B1 | 4/2001 | Ikeda et al. | GB | 2 267 024 | 11/1993 |
| 6,217,690 B1 | 4/2001 | Rajala et al. | GB | 2 268 389 | 1/1994 |
| 6,231,557 B1 | 5/2001 | Krautkramer et al. | IS | 92891 | 2/1992 |
| 6,238,379 B1 | 5/2001 | Keuhn, Jr. et al. | JP | 3-67646 | 3/1991 |
| 6,245,050 B1 | 6/2001 | Odorzynski et al. | WO | WO 80/00676 | 4/1980 |
| 6,245,168 B1 | 6/2001 | Coenen et al. | WO | WO 90/03464 | 4/1990 |
| 6,260,211 B1 | 7/2001 | Rajala et al. | WO | 91/07277 | 5/1991 |
| 6,279,807 B1 | 8/2001 | Crowley et al. | WO | WO 91/15365 | 10/1991 |
| 6,290,979 B1 | 9/2001 | Roe et al. | WO | WO 92/16371 | 10/1992 |
| 6,310,164 B1 | 10/2001 | Morizono et al. | WO | WO 93/15247 | 8/1993 |
| 6,316,013 B1 | 11/2001 | Paul et al. | WO | WO 93/17648 | 9/1993 |
| 6,316,687 B1 | 11/2001 | Davis et al. | WO | WO 94/09736 | 5/1994 |
| 6,316,688 B1 | 11/2001 | Hammons et al. | WO | WO 95/03443 | 2/1995 |
| 6,320,096 B1 | 11/2001 | Inoue et al. | WO | WO 95/04182 | 2/1995 |
| 6,323,389 B1 | 11/2001 | Thomas et al. | WO | WO 95/16425 | 6/1995 |
| 6,329,459 B1 | 12/2001 | Kang et al. | WO | WO 95/16562 | 6/1995 |
| 6,364,863 B1 | 4/2002 | Yamamoto et al. | WO | WO 95/29810 | 11/1995 |
| 6,365,659 B1 | 4/2002 | Aoyama et al. | WO | WO 95/34264 | 12/1995 |
| 6,475,600 B1 | 11/2002 | Morman et al. | WO | WO 96/13989 | 5/1996 |
| 6,537,935 B1 | 3/2003 | Seth et al. | WO | WO 96/23466 | 8/1996 |
| 6,833,179 B2 * | 12/2004 | May et al. ............. 428/212 | WO | WO 96/35402 | 11/1996 |
| 2002/0002021 A1 | 1/2002 | May et al. | WO | WO 97/17046 | 5/1997 |
| 2002/0009940 A1 | 1/2002 | May et al. | WO | WO 98/14156 | 4/1998 |
| 2002/0019616 A1 | 2/2002 | Thomas | WO | WO 98/49988 | 11/1998 |
| 2002/0072561 A1 | 6/2002 | Johoji et al. | WO | WO 98/55062 | 12/1998 |
| 2002/0081423 A1 | 6/2002 | Heffelfinger | WO | WO 99/17926 | 4/1999 |
| 2002/0104608 A1 | 8/2002 | Welch et al. | WO | WO 99/24519 | 5/1999 |
| 2002/0138063 A1 | 9/2002 | Kuen et al. | WO | WO 99/47590 | 9/1999 |
| | | | WO | WO 99/60969 | 12/1999 |
| | | | WO | WO 99/60970 | 12/1999 |
| | | | WO | WO 99/60971 | 12/1999 |

| | | | | | | |
|---|---|---|---|---|---|---|
| WO | WO 00/10500 | 3/2000 | | WO | WO 01/87588 A2 | 11/2001 |
| WO | 00/29199 | 5/2000 | | WO | 02/34184 | 5/2002 |
| WO | WO 00/37003 | 6/2000 | | WO | 02/34511 | 5/2002 |
| WO | WO 00/37005 | 6/2000 | | WO | WO 02/053667 A2 | 7/2002 |
| WO | WO 00/37723 | 6/2000 | | WO | WO 02/053668 A2 | 7/2002 |
| WO | WO 00/59429 | 10/2000 | | WO | 02/060690 | 8/2002 |
| WO | WO 01/00053 | 1/2001 | | WO | WO 02/085624 A1 | 10/2002 |
| WO | 01/32116 | 5/2001 | | WO | WO 2004/005018 A1 | 1/2004 |
| WO | WO 01/45927 A1 | 6/2001 | | WO | WO 2004/039907 A1 | 5/2004 |
| WO | WO 01/49907 | 7/2001 | | | | |
| WO | WO 01/87214 | 11/2001 | | * cited by examiner | | |

METHOD OF MAKING STRAND-REINFORCED ELASTOMERIC COMPOSITES

BACKGROUND OF THE INVENTION

This invention is directed to a method of making elastic composite materials including elastomeric adhesive film reinforced with elastic strands which significantly improves tension decay and adhesion properties of the material.

Personal care garments often include elasticized portions to create a gasket-like fit around certain openings, such as waist openings and leg openings. Laminates made from conventional elastic strands and elastic attachment adhesive are often used to create such elasticized portions. However, such laminates can be rough and uncomfortable. Furthermore, such laminates may cause red-marking on a wearer's skin if the fit is too tight and may result in leakage from the garment if the fit is too loose.

Elastomeric adhesive compositions are multifunctional in the sense that they function as an elastomer in a nonwoven composite while also serving as a hot melt adhesive for bonding substrates. Elastomeric adhesive compositions in the form of elastomeric adhesive films are currently recognized as suitable for use in the manufacture of personal care articles. More particularly, elastomeric adhesive compositions can be used to bond facing materials, such as spunbond, to one another while simultaneously elasticizing the resulting laminate. The resulting laminate can be used to form an elastomeric portion of an absorbent article, such as a region surrounding a waist opening and/or a leg opening.

Non-woven elastic adhesive film laminates may require high output of adhesive add-on to achieve a tension target for product application. High add-on of the film laminate may generate a bulky, thick feel and appearance, and high cost. Furthermore, the high adhesive output requirement for the film formation would make on-line processing even more difficult due to the limitation of hot melt equipment output capacity. Also, such film lamination processes are relatively complex and need more precise control than strand lamination since a film edge thinning effect may cause the film to break during stretching.

Some elastomeric adhesive compositions lose their adhesiveness when the compositions are stretched and then bonded between two nonwoven substrates. The elasticity of these elastomeric adhesive compositions (in terms of tension decay) is negatively affected when laminates including the compositions are aged at elevated temperatures.

One type of elastomeric adhesive composition having improved elastic and adhesion properties that also provides adequate tension for product application is made up of a combination of extruded reinforcing strands and elastomeric adhesive film. A layer of spunbond or other facing material can be laminated along both surfaces of the film to provide elastic composite laminates. The combination of reinforcing strands and the elastomeric adhesive film significantly and advantageously reduces the rate and extent of tension decay, as well as improving adhesion properties of the spunbond laminates compared to spunbond laminates including elastomeric adhesive film without reinforcing strands.

It is known to make such strand-reinforced composites and laminates by extruding the elastomeric adhesive film and the reinforcing strands separately, followed by independent stretching prior to lamination between nonwoven facing materials. However, there are several shortcomings associated with independent stretching of strands and film elements. These shortcomings include a need for more equipment to control/stabilize the process, plus the strands need to be aligned to have uniform spacing. Additionally, frequencies of film or strand break are high especially in high stretch ratio and high web speed. Such drawbacks make the laminate production process difficult and complex.

With the foregoing in mind, it is a feature and advantage of the invention to provide a method of making strand-reinforced elastic composites and laminates with improved processability in which film breakage, strand breakage, and strand alignment problems are minimized or avoided.

SUMMARY OF THE INVENTION

In response to the discussed difficulties and problems encountered in the prior art, a new method of making strand-reinforced elastomeric composites and laminates has been discovered.

The present invention is directed to a method of making strand-reinforced elastic composites, and laminates incorporating such elastic composites. The method provides improved processability and minimization or avoidance of film breakage, strand breakage, and strand alignment problems.

The method of the invention includes casting an elastomeric adhesive film onto a chill roll. The film may be passed onto a second chill roll. In any case, a plurality of elastic strands is extruded onto the film while the film is on a chill roll to create a strand-reinforced composite. The strand-reinforced composite is then stretched, suitably by at least 200%. The stretched composite can be laminated between two facing sheets to form a strand-reinforced composite laminate.

Stretching the film and strand components as a single unit affords the added benefits of a more robust manufacturing method. The ability to control processability is especially critical for converting line operations where start/stop situations need to be minimized for economic reasons. Furthermore, by extruding the elastic strands directly onto the film, the strands are self-aligning on the film in the machine direction without moving in the cross direction or breaking. While the film reinforces the strands, the strands also provide reinforcement to the film, especially along the edges of the film. The elastic composite made from the mutually reinforced strand and film combination is much stronger and resistant to breaking than elastomeric adhesive film alone or elastic strands alone. Additionally, the composite made according to the method of the invention can be stretched even higher and the web speed can be run even faster than strand-reinforced elastomeric composites made by separately stretching the film and the strands, with a lesser chance of film or strand breakage or strand alignment problems.

The method of the invention is simplified, compared to methods that involve separate stretching of the film and the strands. The simplified process is important for ensuring quality and productivity for high speed manufacturing operations. Also, the method of the invention is designed to work on a converting line using film and strand material supplied from melt tanks as well as off-line where strand and/or film roll material may be extruder processable.

Tension and retraction properties of the composites can be tuned by varying the ratio of strands to film amount as well as controlling the amount of stretch of the single unit composite. Tension may also be controlled and enhanced through selection of the film composition, selection of the strand composition, selection of the substrate, the add-on rate, and combinations of any of these controlling factors, without risking web breakage problems and without encountering strand misalignment issues.

With the foregoing in mind, it is a feature and advantage of the invention to provide a method of making strand-reinforced elastomeric composites and laminates with enhanced productivity and quality in view of a reduction or elimination of web and/or strand breaks, and strand self-alignment.

DEFINITIONS

Figure 1:
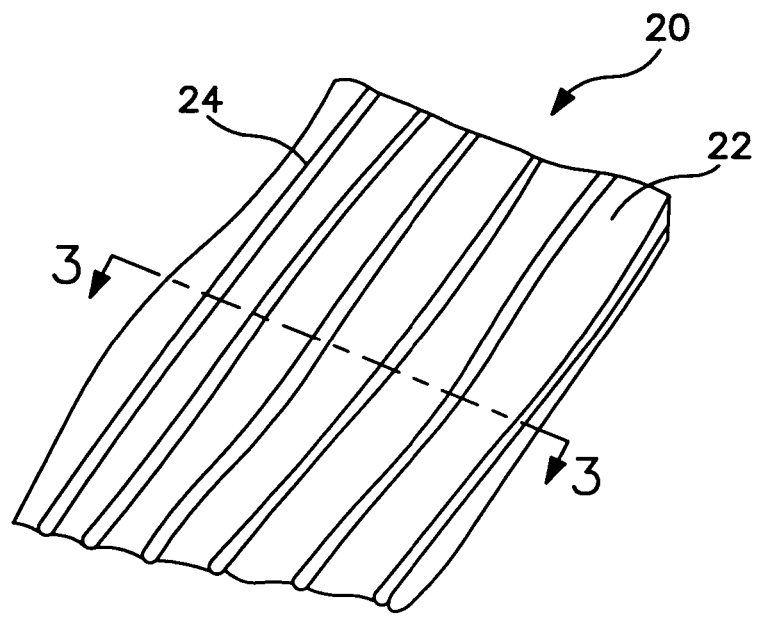
FIG. 1 is a plan view of one embodiment of an elastic composite made according to the method of the invention.

Within the context of this specification, each term or phrase below will include the following meaning or meanings.

"Bonded" refers to the joining, adhering, connecting, attaching, or the like, of at least two elements. Two elements will be considered to be bonded together when they are bonded directly to one another or indirectly to one another, such as when each is directly bonded to intermediate elements.

"Elastic tension" refers to the amount of force per unit width required to stretch an elastic material (or a selected zone thereof) to a given percent elongation.

"Elastomeric" and "elastic" are used interchangeably to refer to a material or composite that is generally capable of recovering its shape after deformation when the deforming force is removed. Specifically, as used herein, elastic or elastomeric is meant to be that property of any material which, upon application of a biasing force, permits the material to be stretchable to a stretched biased length which is at least about 50 percent greater than its relaxed unbiased length, and that will cause the material to recover at least 40 percent of its elongation upon release of the stretching force.

A hypothetical example which would satisfy this definition of an elastomeric material would be a one (1) inch sample of a material which is elongatable to at least 1.50 inches and which, upon being elongated to 1.50 inches and released, will recover to a length of less than 1.30 inches. Many elastic materials may be stretched by much more than 50 percent of their relaxed length, and many of these will recover to substantially their original relaxed length upon release of the stretching force.

"Elongation" refers to the capability of an elastic material to be stretched a certain distance, such that greater elongation refers to an elastic material capable of being stretched a greater distance than an elastic material having lower elongation.

"Extruded" refers to a material that is processed through an extrusion die or a slot coat die connected to an extruder or a melt tank.

"Film" refers to a thermoplastic film made using a film extrusion process, such as a cast film or blown film extrusion process. The term includes apertured films, slit films, and other porous films which constitute liquid transfer films, as well as films which do not transfer liquid.

"Garment" includes personal care garments, medical garments, and the like. The term "disposable garment" includes garments which are typically disposed of after 1-5 uses. The term "personal care garment" includes diapers, training pants, swim wear, absorbent underpants, adult incontinence products, feminine hygiene products, and the like. The term "medical garment" includes medical (i.e., protective and/or surgical) gowns, caps, gloves, drapes, face masks, and the like. The term "industrial workwear garment" includes laboratory coats, cover-alls, and the like.

"Layer" when used in the singular can have the dual meaning of a single element or a plurality of elements.

"Machine direction" as applied to a film, refers to the direction on the film that was parallel to the direction of travel of the film as it left the extrusion or forming apparatus. If the film passed between nip rollers or chill rollers, for instance, the machine direction is the direction on the film that was parallel to the surface movement of the rollers when in contact with the film. "Cross direction" refers to the direction perpendicular to the machine direction. Dimensions measured in the cross direction are referred to as "width" dimensions, while dimensions measured in the machine direction are referred to as "length" dimensions.

"Meltblown fiber" refers to fibers formed by extruding a molten thermoplastic material through a plurality of fine, usually circular, die capillaries as molten threads or filaments into converging high velocity gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface.

"Mutually-reinforced" refers to a laminate in which each component provides reinforcement to the other component(s).

"Nonwoven" and "nonwoven web" refer to materials and webs of material having a structure of individual fibers or filaments which are interlaid, but not in an identifiable manner as in a knitted fabric. The terms "fiber" and "filament" are used herein interchangeably. Nonwoven fabrics or webs have been formed from many processes such as, for example, meltblowing processes, spunbonding processes, air laying processes, and bonded carded web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.)

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Spunbond fiber" refers to small diameter fibers which are formed by extruding molten thermoplastic material as filaments from a plurality of fine capillaries of a spinnerette having a circular or other configuration, with the diameter of the extruded filaments then being rapidly reduced as taught, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Strand" refers to an article of manufacture whose width is less than a film and is suitable for incorporating into a film, according to the present invention.

"Stretchable" means that a material can be stretched, without breaking, by at least 50% (to at least 150% of its initial (unstretched) length) in at least one direction, suitably by at least 100% (to at least 200% of its initial length), desirably by at least 150% (to at least 250% of its initial length). The term includes elastic materials as well as materials that stretch but do not significantly retract. The percentage stretch of strands and films is calculated by the percentage difference between a primary chill roll speed and a final nip roll speed. For example, in FIG. 4, if the first chill roller 40 is running at a speed of x and the nip rollers 52 and 54 are running at a speed of 6x, the strands and/or film being stretched between the first chill roller 40 and the nip rollers 52, 54 are being stretched 600%.

"Thermoset" describes a material that is capable of becoming permanently cross-linked, and the physical form of the material cannot be changed by heat without the breakdown of chemical bonds.

"Vertical filament stretch-bonded laminate" or "VF SBL" refers to a stretch-bonded laminate made using a continuous vertical filament process, as described herein.

These terms may be defined with additional language in the remaining portions of the specification.

DETAILED DESCRIPTION OF THE PRESENTLY PREFERRED EMBODIMENTS

The present invention is directed to a simplified method of making strand-reinforced elastic composites and laminates having superior elastic and adhesion properties. The composites and laminates can be incorporated into any suitable article, such as personal care garments, medical garments, and industrial workwear garments. More particularly, the elastic composites and elastic composite laminates are suitable for use in diapers, training pants, swim wear, absorbent underpants, adult incontinence products, feminine hygiene products, protective medical gowns, surgical medical gowns, caps, gloves, drapes, face masks, laboratory coats, and coveralls.

A number of elastomeric components are known for use in the design and manufacture of such articles. For example, disposable absorbent articles are known to contain elasticized leg cuffs, elasticized containment flaps, elasticized waist portions, and elasticized fastening tabs. The elastic composites and laminates made according to the method of this invention may be applied to any suitable article to form such elasticized areas.

As shown in FIG. 1, an elastomeric composite 20 made according to the method of the invention includes an elastomeric adhesive film 22 with a number of elastic reinforcing strands 24 adhered to and partially embedded therein.

Figure 2:
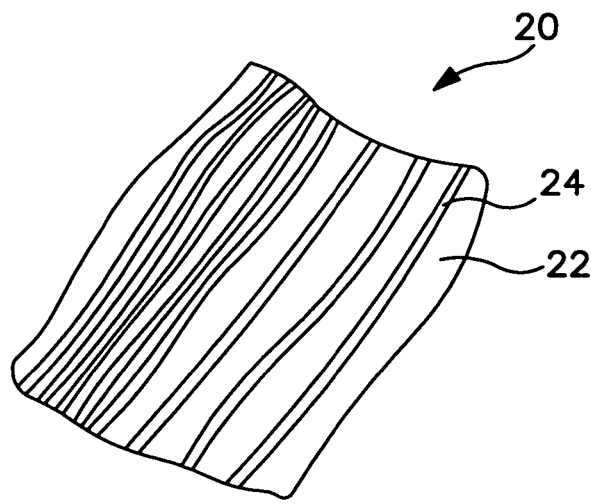
FIG. 2 is a plan view of another embodiment of an elastic composite made according to the method of the invention.
Figure 3:
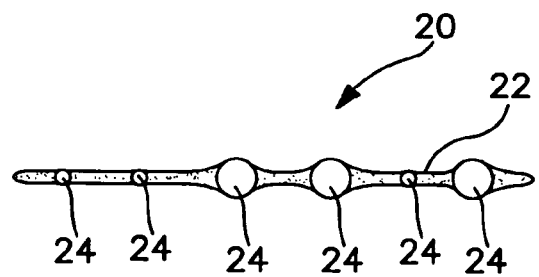
FIG. 3 is a cross-sectional view, taken along line 3-3 of FIG. 1, of another embodiment of an elastic composite made according to the method of the invention.

It will be appreciated that the strands 24 may be laid out periodically, non-periodically, and in various spacings, groupings, and sizes, according to the effect desired from the composite 20 and the use to which it is put. As shown in FIG. 2, for example, a group of strands 24 in one region of the composite 20 can be spaced apart much more closely than another group of strands 24, resulting in greater tension in the region in which the strands 24 are more closely spaced. As another example, FIG. 3 illustrates a cross-sectional view of the composite 20 having unequally sized elastic strands 24 with some strands having a larger diameter, and thus higher tension, than others. While referred to as being of different diameter, it will be appreciated that the strands 24 need not be circular in cross-section within the context of this invention. Furthermore, the strands 24 of different size or composition may be intermingled within groupings in regular or irregular patterns.

The elastomeric adhesive film 22 is suitably made up of an elastomeric, hot melt, pressure-sensitive adhesive having an adhesive bond strength, as determined by the test method set forth below, of at least 50 grams force per inch (2.54 cm) width, suitably of at least 100 grams force per inch (2.54 cm) width, alternatively of at least 300 grams force per inch (2.54 cm) width, alternatively of at least from about 100 grams force per inch (2.54 cm) width to about 400 grams force per inch width. An example of a suitable elastomeric adhesive film 22 may be made up of 35 wt % PICOLYTE S115 and 65 wt % KRATON G2760. The elastomeric, hot melt, pressure-sensitive adhesive may be applied to a chill roll or similar device, in the form of a strand or ribbon. The strand or ribbon is then minimally stretched and thinned to form the film 22. The film suitably has a thickness of about 0.001 inch (0.025 mm) to about 0.05 inch (1.27 mm), alternatively of from about 0.001 inch (0.025 mm) to about 0.01 inch (0.25 mm), and a width of from about 0.05 inch (1.27 mm) to about 3.0 inches (7.62 cm), alternatively of from about 0.5 inch (1.27 cm) to about 1.5 inches (3.81 cm). The elastomeric, adhesive film 22 may also be capable of imparting barrier properties in an application.

Suitable elastomeric, hot melt, pressure-sensitive adhesives from which the elastomeric adhesive film 22 may be made include elastomeric polymers, tackifying resins, plasticizers, oils and antioxidants.

One particular formulation of the elastomer adhesive film 22 includes a base polymer and a tackifier resin. The composition may also include additional additives. The choice of polymer and tackifier is important, as is the ratio of polymer or copolymers to tackifier. Another important consideration is the ratio of additives to tackifier.

The base polymer suitably has a styrene content of between about 15% and about 45%, or between about 18% and about 30%, by weight of the base polymer. The base polymer may achieve the styrene content either by blending different polymers having different styrene co-monomer levels or by including a single base polymer that has the desired styrene co-monomer level. Generally, the higher the styrene co-monomer level is, the higher the tension is.

The base polymer may include polystyrene-polyethylene-polypropylene-polystyrene (SEPS) block copolymer, styrene-isoprene-styrene (SIS), styrene-butadiene-styrene (SBS) block copolymer, as well as combinations of any of these. One example of a suitable SEPS copolymer is available from Kraton Polymers of Belpre, Ohio, under the trade designation KRATON® G 2760. One example of a suitable SIS copolymer is available from Dexco, a division of Exxon-Mobil, under the trade designation VECTOR™. Suitably, the film composition includes the base polymer in an amount between about 30% and about 65% by weight of the composition.

The tackifier may include hydrocarbons from petroleum distillates, rosin, rosin esters, polyterpenes derived from wood, polyterpenes derived from synthetic chemicals, as well as combinations of any of these. A key element of the film composition is a tackifier. An example of a suitable tackifier is available from Hercules Inc. of Wilmington, Del., under the trade designation PICOLYTE™ S115. Suitably, the composition includes the tackifier in an amount between about 30% and about 70% by weight of the composition.

Other additives may be included in the film composition as well. In addition to the adhesion provided by the tackifier, various additives may provide instantaneous surface tackiness and pressure sensitive characteristics as well as reduced melt viscosity. One example of a particularly suitable low softening point additive is PICOLYTE™ S25 tackifier, available from Hercules Inc., having a softening point in a range around 25 degrees Celsius, or paraffin wax having a melting point of about 65 degrees Celsius may also be used.

Additionally, an antioxidant may be included in the film composition, suitably in an amount between about 0.1% and about 1.0% by weight of the composition. One example of a suitable antioxidant is available from Ciba Specialty Chemicals under the trade designation IRGANOX™ 1010.

The elastomeric adhesive film 22 suitably has an elongation of at least 50 percent, alternatively of at least 150 percent, alternatively of from about 50 percent to about 200 percent, and a tension force of less than about 400 grams force per inch (2.54 cm) width, alternatively of less than about 275 grams force per inch (2.54 cm) width, alternatively of from about 100 grams force per inch (2.54 cm) width to about 250 grams force per inch (2.54 cm) width. Tension force, as used herein, is determined one minute after stretching the film to 100% elongation. A method for determining elongation is described in detail below.

The elastomeric adhesive film 22 is capable not only of introducing a degree of elasticity to facing materials but is also capable of providing a construction adhesive function. That is, the film 22 adheres together the facing materials or other components with which it is in contact. It is also possible that the film does not constrict upon cooling but, instead, tends to retract to approximately its original dimension after being elongated during use in a product.

Materials suitable for use in preparing the elastic reinforcing strands 24 include raw polymers, a mixture of polymers, as well as tackified polymers. More specifically, the elastic reinforcing strands 24 may include diblock, triblock, tetrablock, or other multi-block elastomeric copolymers such as olefinic copolymers, including ethylene-propylene-diene monomer (EPDM), styrene-isoprene-styrene (SIS), styrene-butadiene-styrene (SBS), styrene-ethylene/butylene-styrene (SEBS), or styrene-ethylene/propylene-styrene (SEPS), which may be obtained from the Kraton Polymers of Belpre, Ohio, under the trade designation KRATON® elastomeric resin or from Dexco, a division of Exxon-Mobil, under the trade designation VECTOR® (SIS polymers); polyurethanes, including those available from E. I. Du Pont de Nemours Co., under the trade name LYCRA® polyurethane; polyamides, including polyether block amides available from Ato Chemical Company, under the trade name PEBAX® polyether block amide; polyesters, such as those available from E. I. Du Pont de Nemours Co., under the trade name HYTREL® polyester; polyisoprene; cross-linked polybutadiene; and single-site or metallocene-catalyzed polyolefins having density less than about 0.89 grams/cubic centimeter, available from Dow Chemical Co. under the trade name AFFINITY®. The elastic reinforcing strands 24 may also include a tackifier. The tackifier may include hydrocarbons from petroleum distillates, rosin, rosin esters, polyterpenes derived from wood, polyterpenes derived from synthetic chemicals, as well as combinations of any of these.

A number of block copolymers can also be used to prepare the elastic reinforcing strands 24 used in this invention. Such block copolymers generally include an elastomeric mid-block portion B and a thermoplastic endblock portion A. The block copolymers may also be thermoplastic in the sense that they can be melted, formed, and resolidified several times with little or no change in physical properties (assuming a minimum of oxidative degradation). Alternatively, the elastic strands 24 can be made of a polymer that is not thermally processable, such as LYCRA® spandex, available from E. I. Du Pont de Nemours Co., or cross-linked natural rubber in film or fiber form. Thermoset polymers and polymers such as spandex, unlike the thermoplastic polymers, once cross-linked cannot be thermally processed, but can be obtained on a spool or other form and can be stretched and applied to the strands in the same manner as thermoplastic polymers. As another alternative, the elastic strands 24 can be made of a thermoset polymer, such as AFFINITY®, available from Dow Chemical Co., that can be processed like a thermoplastic, i.e. stretched and applied, and then treated with radiation, such as electron beam radiation, gamma radiation, or UV radiation to cross-link the polymer, or use polymers that have functionality built into them such that they can be moisture-cured to cross-link the polymer, thus resulting in a polymer and the enhanced mechanical properties of a thermoset.

Endblock portion A may include a poly(vinylarene), such as polystyrene. Midblock portion B may include a substantially amorphous polyolefin such as polyisoprene, ethylene/propylene polymers, ethylene/butylenes polymers, polybutadiene, and the like, or mixtures thereof.

Suitable block copolymers useful in this invention include at least two substantially polystyrene endblock portions and at least one substantially ethylene/butylenes mid-block portion. A commercially available example of such a linear block copolymer is available from Kraton Polymers under the trade designation KRATON® G1657 elastomeric resin. Another suitable elastomer is KRATON® G2760. Yet another suitable elastomer is an SIS triblock copolymer available from Dexco, a division of Exxon-Mobil, under the trade designation VECTOR®.

The elastic reinforcing strands 24 may also contain blends of elastic and inelastic polymers, or of two or more elastic polymers, provided that the blend exhibits elastic properties. The strands 24 are substantially continuous in length. The strands 24 may have a circular cross-section but, as previously mentioned, may alternatively have other cross-sectional geometries such as elliptical, rectangular, triangular or multi-lobal. In one embodiment, one or more of the elastic reinforcing strands 24 may be in the form of elongated, rectangular strips produced from a film extrusion die having a plurality of slotted openings.

The ratio of film to strands in the composite may be adjusted to control tension in the composite. For example, the elastic strands may account for between about 5% and about 50%, or between about 10% and about 35%, or between about 15% and about 25% by weight of the composite.

Figure 4:
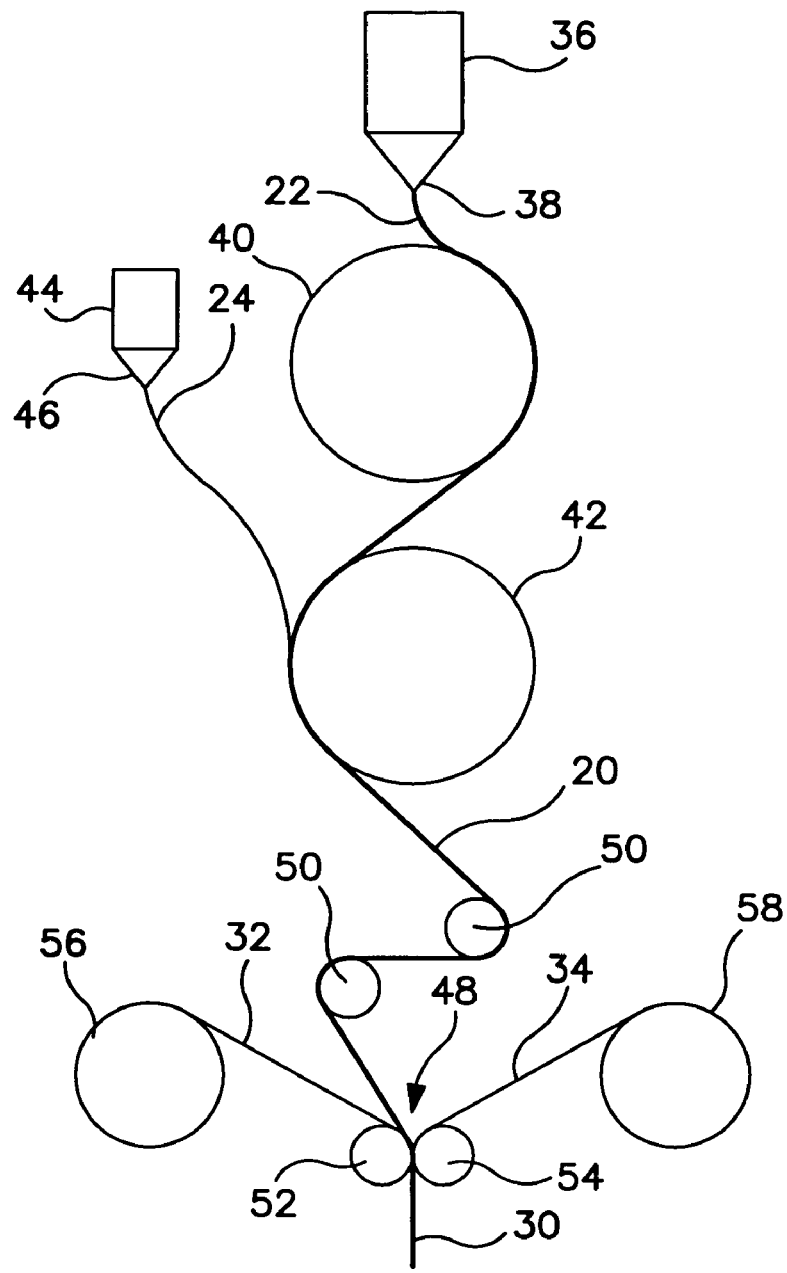
FIG. 4 illustrates one embodiment of the method of the invention.

FIG. 4 illustrates a method and apparatus for making a strand-reinforced elastic composite as described above. While FIG. 4 illustrates a composite VF SBL process it will be appreciated that other processes consistent with the present invention may be used. A melt tank 36 using a slotted film die 38, for example, produces the elastomeric adhesive film 22 which is cast onto a first chill roll 40 and passed to a second roll 42, such as a second chill roll. An extruder 44 produces reinforcing strands of elastic material 24 through a filament die 46. The strands 24 are extruded onto the film 22 while the film is in contact with the second roll 42, thereby creating a strand-reinforced composite 20 on the second roll 42. The composite 20 is stretched as a single unit while conveyed vertically towards a nip 48 by one of more fly rollers 50. The nip 48 is formed by opposing first and second nip rollers 52, 54. For example, the composite may be stretched between about 200% and about 1200%, or between about 400% and about 1000%. Another process parameter is the add-on rate. More specifically, the elastic strands may be adhered to, and partially embedded in, the elastomeric adhesive film at an add-on rate of between about 5 and about 50 grams per square meter before stretching.

By stretching the composite 20 as a unit, namely with the film 22 and strands 24 combined, as opposed to stretching the film and the strands separately, a more robust manufacturing method can be carried out. More particularly, the strands 24 and the film 22 reinforce one another, thereby minimizing or avoiding film breakage and strand breakage. Thus, the composite 20 may be considered a mutually-reinforced strand/film composite. Strand alignment problems are also minimized or avoided because the method of the invention forces the strands 24 to align themselves on the film 22 in the machine direction without moving in the cross direction or breaking. The alignment of the strands 24 also reinforces the film 22, especially along the edges of the film.

The mutually reinforced strand and film combination allows the composite 20 to be stretched considerably during the process, and the web speed can be run at a considerably high speed. Furthermore, the process is essentially simplified, which is important for ensuring quality and productivity for high-speed manufacturing operations. The ability to control processability is especially critical for converting line operations where start/stop situations need to be minimized for economic reasons.

Figure 5:
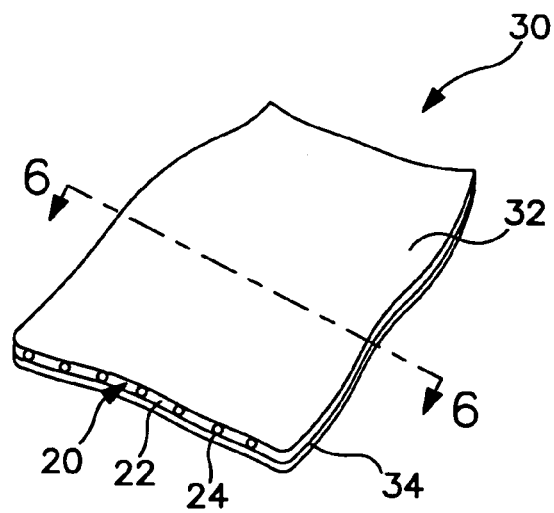
FIG. 5 is a plan view of one embodiment of an elastic composite laminate made according to the method of the invention.
Figure 6:
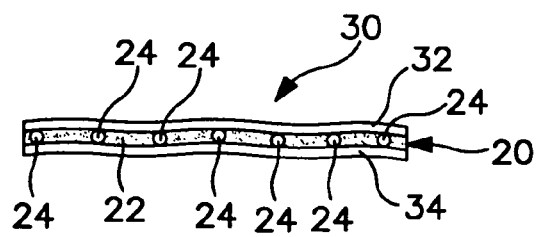
FIG. 6 is a cross-sectional view, taken along line 6-6 of FIG. 5, of another embodiment of an elastic composite laminate made according to the method of the invention.

A strand-reinforced elastomeric composite laminate 30, or mutually-reinforced elastomeric strand/film composite laminate, may be formed by laminating a first facing sheet 32 and a second facing sheet 34 to opposite surfaces of the stretched elastomeric composite 20. Examples of such laminates 30 are illustrated in FIGS. 5 and 6. Facing materials may be formed using conventional processes, including the spunbond and meltblowing processes described in the DEFINITIONS. For example, the facing sheets 32, 34 may each include a spunbonded web having a basis weight of about 0.1-4.0 ounces per square yard (osy), suitably 0.2-2.0 osy, or about 0.4-0.6 osy. As another example, the facing sheets 32, 34 may each include a non-porous polyolefin film, such as outer cover material, or a combination of film and spunbond material. Two or more facing sheets 32, 34 may be present in the laminate 30. The facing sheets 32, 34 may include the same or similar materials or different materials. Examples of suitable types of facing sheet 32, 34 combinations include at least one sheet of spunbond and at least one sheet of film, or two sheets of film, or two sheets of spunbond.

If the facing sheets 32, 34 are to be applied to the composite 20 without first being stretched, the facing sheets may or may not be capable of being stretched in at least one direction in order to produce an elasticized area. For example, the facing sheets 32, 34 could be necked, or gathered, in order to allow them to be stretched after application of the elastic composite 20. Various post treatments, such as treatment with grooved rolls, which alter the mechanical properties of the material, are also suitable for use.

In order to form the elastic composite laminate 30, first and second rolls 56 and 58, respectively, of spunbond facing material or other suitable facing material are fed into the nip 48 on either side of the elastic composite, as shown in FIG. 4, and are bonded by the adhesive present in the elastic composite. The facing material might also be made in situ rather than unrolled from previously-made rolls of material. While illustrated as having two lightweight gatherable spunbond facings, it will be appreciated that only one facing material, or various types of facing materials, may be used.

Tension and retraction properties within the elasomeric composite 20 or laminate 30 may be controlled, or tuned, during the process through percentage stretch of the composite prior to adhesion to the facing sheets, through the ratio of strands to film, and/or through the amount of strand add-on or thickness, with greater stretch and greater add-on or thickness each resulting in higher tension. Tension can also be controlled through selection of the film composition, selection of the strand composition, substrate selection, and/or by varying strand geometries and/or spacing between strands.

The method of the invention is designed to work on the converting line using film and/or strand material supplied from melt tanks as well as off-line where strands and/or film material obtained on a supply roll, or other method of storage, may be extruder processable.

Figure 7:
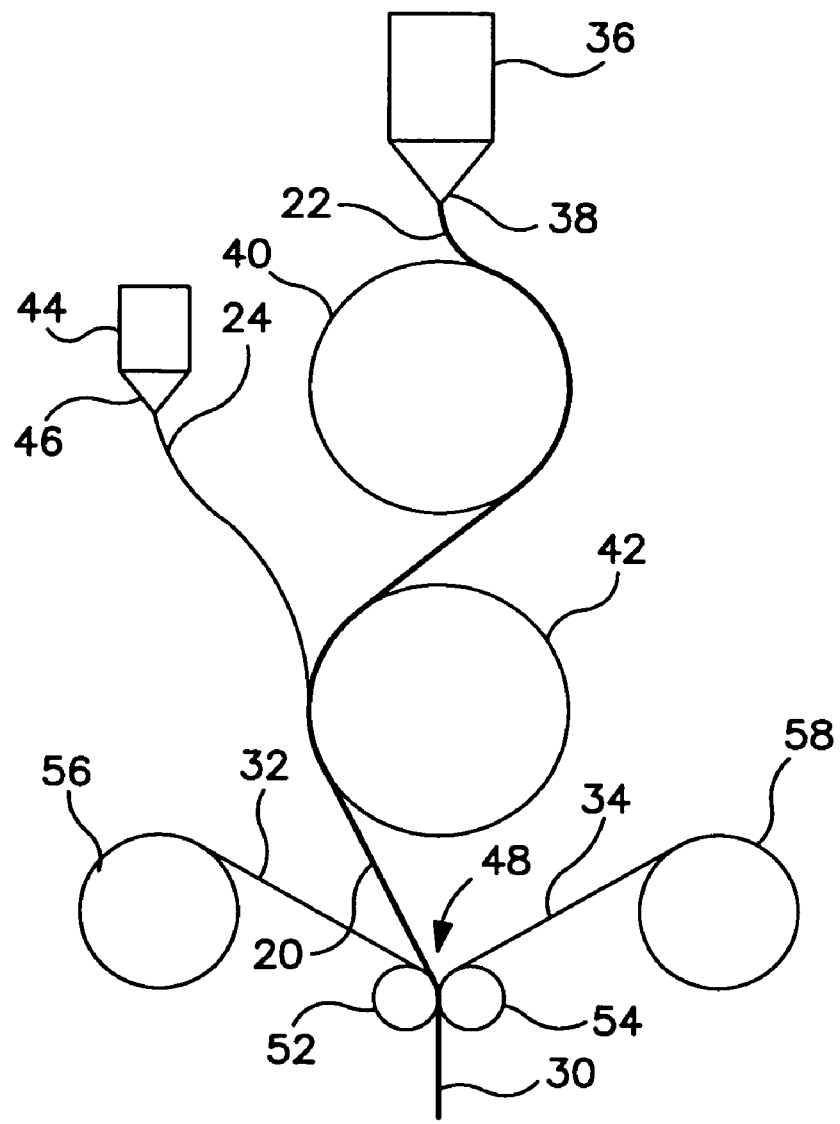
FIG. 7 is a schematic view of another embodiment of the method of the invention.

FIG. 7 illustrates a VF SBL process in which no fly rollers 50 are used. Instead, the elastomeric adhesive film 22 is extruded onto chill roller 40 and is passed to chill roller 42. The strands 24 are extruded onto chill roller 42 on top of the film 22 thereby forming the strand-reinforced composite 20. The composite 20 is stretched between the chill rollers 42 and the nip 48. Except for the lack of fly rollers, the processes of FIGS. 4 and 7 are similar. In either case, the strands 24 and the elastomeric adhesive film 22 together are laminated between a first facing layer 32 and a second facing layer 34 at the nip 48.

Figure 8:
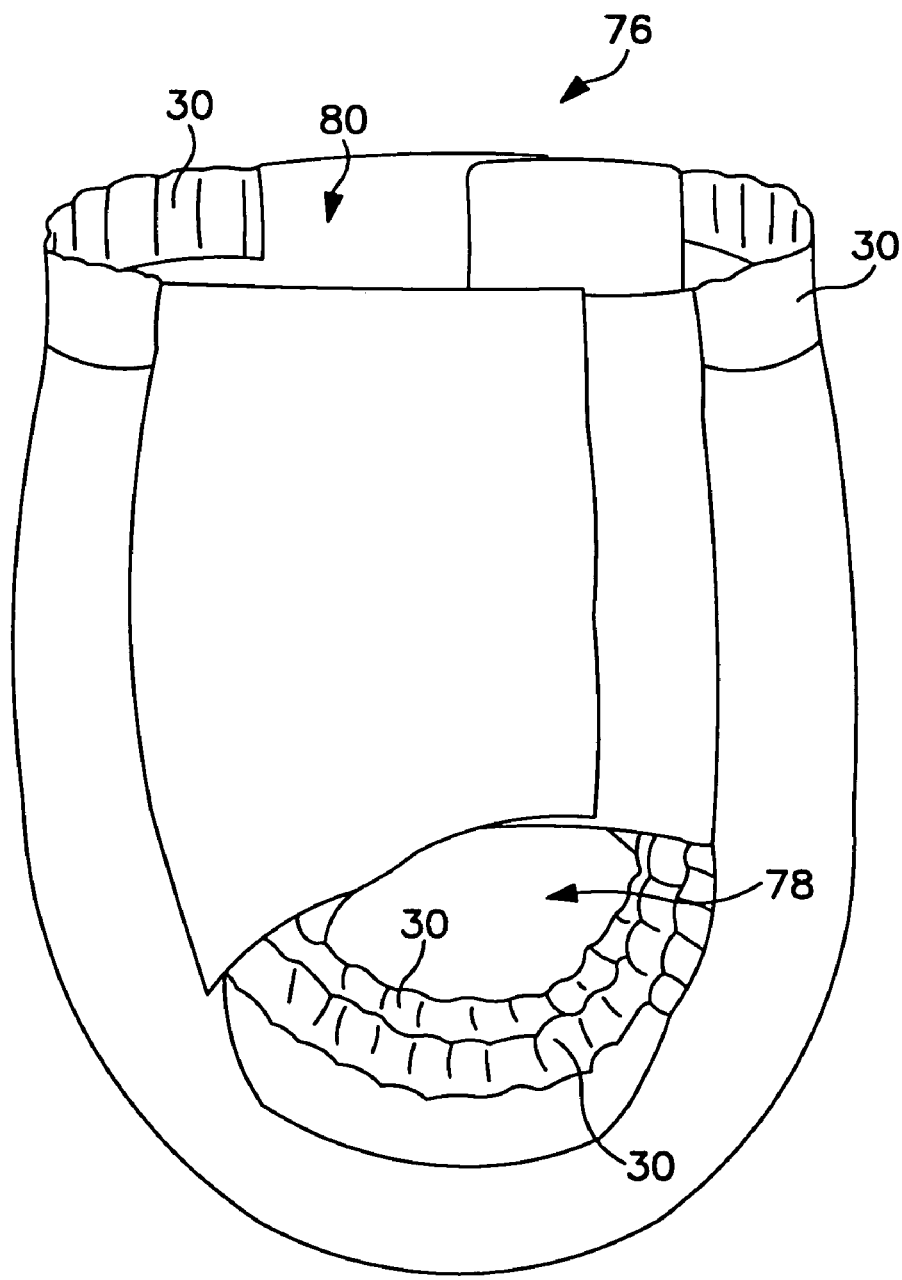
FIG. 8 is a perspective view of a garment having an elastic composite laminate around the leg openings and waist opening.

The resulting elastic composites and elastic composite laminates are considerably strong and resistant to breaking and are therefore particularly useful in providing elasticity in personal care absorbent garments 76, as shown in FIG. 8. More specifically, as shown in FIG. 8, the elastic composite laminates 30 are particularly suitable for use in providing a gasket-like fit around leg openings 78 and waist openings 80. The laminates of this invention are less likely to undergo tension decay or delamination compared to similar laminates lacking the reinforcing strands. Furthermore, the reinforcing strands enable the composite tension to be tunable while preserving the soft feel and aesthetic properties of the laminate. Thus, elastic composite laminates can be produced with a desired fit or gasket-like quality without causing red marks on a wearer's skin due to excessive tension, while preserving the soft and gentle feel and improved adhesion of the laminate.

Figure 9:
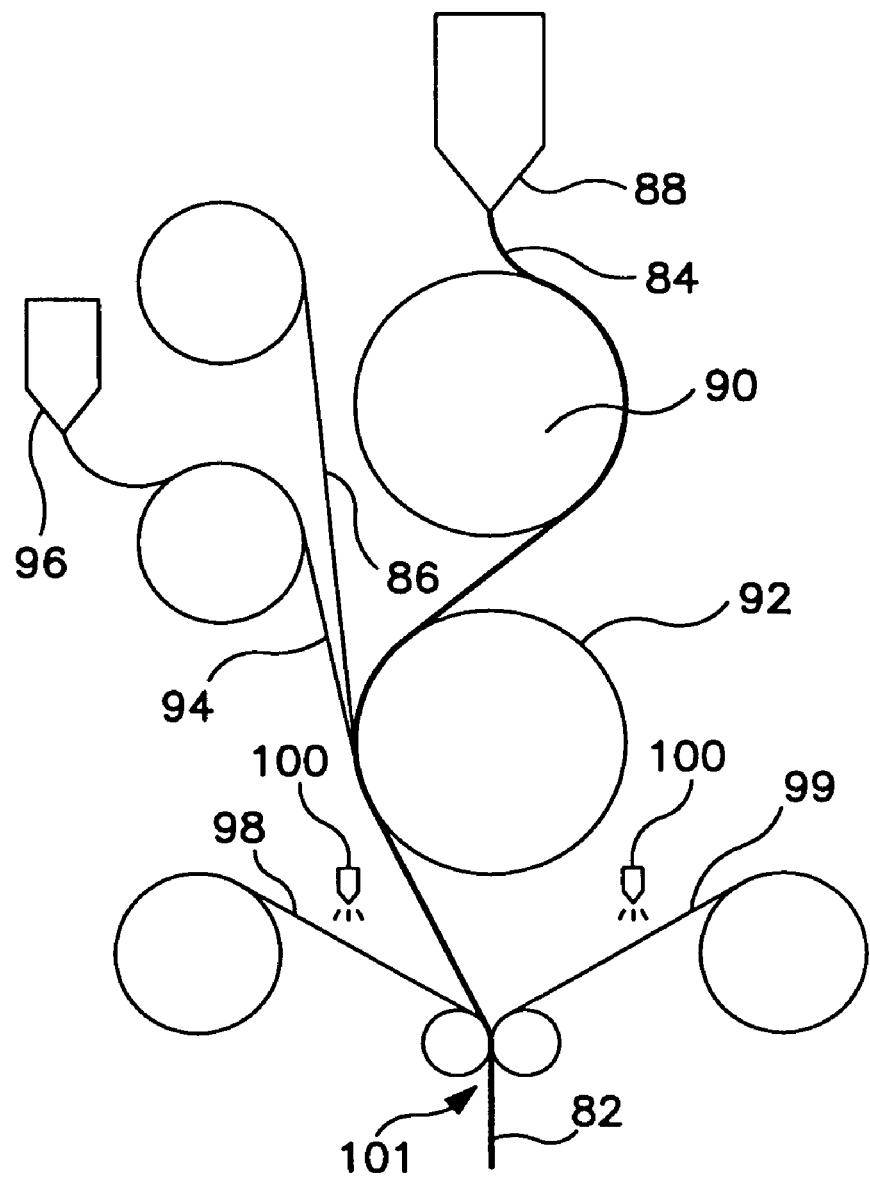
FIG. 9 is a schematic view of another embodiment of the method of the invention.

In another embodiment of the invention, illustrated in FIG. 9, a biaxial stretch laminate 82 may be formed by casting a film 84 through a first film die 88 onto a first roll 90, stretching the film, and spinning and stretching a plurality of strands 86 onto the film while the film is stretched. The method may also include thinning, necking, and/or heat-treating the film. The film may also be second-stretched, or stretched a second time. The strands may also be heat-treated and/or second-stretched. Alternatively, ribbons of film rather than strands may be stretched and adhered to the stretched film. As another alternative, both ribbons of film and strands may be adhered to the film. The stretching steps create thinner films or strands, resulting in laminates that are thinner overall. Furthermore, by warming the film 84 on the first roll 90, stretching the film, cooling the film on a second roll 92, and stretching the film again, a necked elastic film may be created.

A second film 94 may be cast through a second film die 96 over the strands or ribbons 86 on top of the first film 84 as the first film is stretched, thereby encapsulating the strands 86 between film layers 84, 94. The second film 94 may instead be a foam, or a foamed film, that is foamed inline on top of the first film and strands. Polyurethane film does not set up right away and would therefore foam easily.

Additionally, one or more facing materials 98, 99 may be laminated to the film or films. The facing material(s) may include any of the previously discussed facing materials, such as a necked material. The laminate 82 resulting from this embodiment of the method of the invention may have different stretch in the machine direction than in the cross direction. Furthermore, the laminates may be "zoned," with different elastic properties along the length and/or width of the laminate which may be created through zoning the film and/or the strands. Additionally, adhesive 100 used to bond the facing materials 98, 99 to the film may be zoned to create additional functionality.

The film 84, 94 in this embodiment need not be limited to elastomeric adhesive films, but instead may include any suitable elastomeric film, or even a foamed elastomer such as polyurethane. The film may be filled with calcium carbonate, for example, or any other suitable filler to impart breathability to the film upon stretching. The strands 86 may include strands of elastomer, for example, such as any of the strand materials described in the previous embodiments.

Most laminates currently have one layer of elastomeric material or at most two that are integrated upon extrusion and not handled separately green before they are integrated together. As used herein, the term "green" refers to a material that has never been rolled up or otherwise placed in storage. The ability to handle the film and strands or film ribbons and strands or strand and foams separately, but in the same process, provides benefits to forming new elastic structures beyond those currently practiced.

Similar to the embodiments described above, by fixing the strands 86 onto the green film 84 the occurrence of strand slippage is greatly reduced. Since the film is pressure-sensitive and tacky when the strands are applied to the film, the need for adhesive between the film 84 and the strands 86 is eliminated, and, in addition, strand slippage is prevented. Additionally, the strands 86 may be at least partially embedded in, or encapsulated by, the layer of green film 84.

Another advantage of this embodiment is that the cast and annealing rolls 90, 92 in the process can be run independent of each other in terms of temperature and speed, which means that the elastic film 84 can be annealed or cooled as desired to introduce properties such as latency, deadening of the elastic, or even enhancing the setting of the elastomer for more immediate elastic properties.

Another benefit of this embodiment is the point at which the facings 98, 99 are introduced into the process. If the first facing 98 is laminated to the elastic film/strand layer on the second roll 92 and the second facing 99 is laminated later at the nip point 101, then a two stretch-to-stop laminate can be generated. A laminate having two stretch-to-stop points has unique properties.

The material resulting from this embodiment of the invention can be used for side panels, ears, waist bands, leg elastics, and the like, or for outer covers incorporating elastic and breathable properties. Any of the elements of this embodiment can be combined with any of the elements of the preceding embodiments.

In yet another embodiment of the invention, the invention includes a multi-layer elastic or at least extensible laminate made from film (filled or monolithic) and fibers with possible subsequent lamination to at least one facing material which may be a necked material, a mesh material, or other substrate to form a biaxial stretch laminate. The laminate may have different stretch properties in the machine direction than in the cross direction. The film can be either continuous or discontinuous, such as in the form of ribbons.

Figure 10:
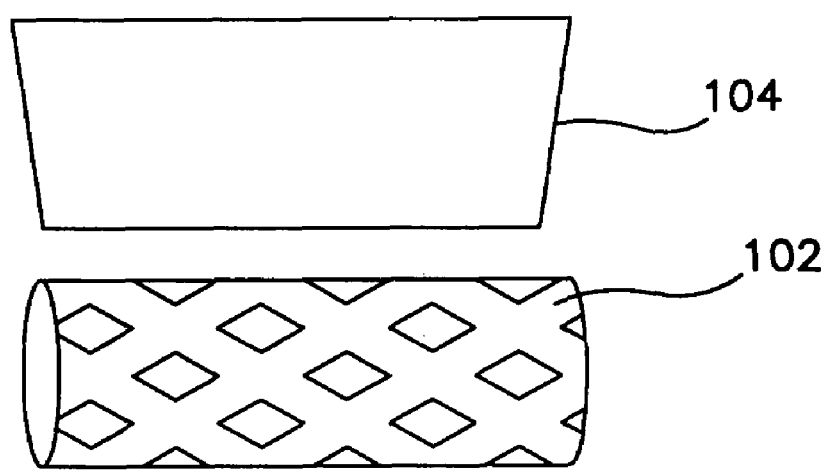
FIG. 10 is a schematic view of a lattice-design roller that can be used to produce a mesh layer in yet another embodiment of the invention.

In one particular embodiment, for example, the laminate may include an extensible film, filled with calcium carbonate or other suitable filler to provide breathability upon stretching. The laminate may also include an inherently extensible or elastic nonwoven layer, such as a bicomponent spunbond web, or adhesively laminated layers of such materials. Between the film and the nonwoven layers is an extruded elastic mesh structure, which can be made with an elastomer and can also provide bias stretch due to the structure. An illustration of apparatus for creating the mesh layer is provided in FIG. 10. More particularly, the apparatus includes a patterned roll 102 onto which the elastomer is extruded from a film die 104. This laminate structure has the advantage of using a film layer that can be formulated to meet breathability targets without the additional burden of being elastic by essentially decoupling elastic and breathability requirements for the film. The mesh structure is essentially an extruded layer so there is flexibility in resin choice, mesh structure, and the like.

In another particular embodiment, for example, the laminate may include a breathable cross-direction-extensible film, or a very low basis weight monolithic film, with an elastomer printed onto a surface of the film in stripes or bars. The elastomer provides sufficient stretch and recovery. The film is then laminated to an inherently extensible and/or elastic film.

In yet another particular embodiment, for example, the laminate may include a 3-layer film with outer film layers that are breathable and extensible or elastic and a middle layer of elastic strands between the two outer film layers. Facing sheets are either adhesively or thermally bonded to the outer film layers. Each of the film layers is extruded through a die, with the middle layer extruded through a die designed to create strips or ribbons of elastomer. If the two outer film layers do not fully marry, or bond to one another across the entire contact surface, gaps are formed which may serve as a built-in spacer layer. Alternatively, the outer film layers may be treated with a humectant or water-vapor-absorbing coating or particulate on the surface in contact with the middle layer to minimize water vapor transfer through the laminate, thereby potentially eliminating dampness concerns at high breathability levels.

These laminates are particularly suitable for providing outer covers with breathability, cross-direction extensibility, and possibly dampness control. Any of the elements of this embodiment can be combined with any of the elements of the preceding embodiments.

In still another embodiment of the invention, a machine capable of carrying out both vertical filament laminate (VFL) processes and neck bonded laminate (NBL) processes can be used to carry out any of the methods of the invention. Because the two processes are so similar, this combination machine results in lower capital cost and increased asset flexibility compared to having two separate machines. This machine has unique characteristics that allow it to process machine direction, cross direction and bi-axial stretch materials.

Both NBL and VFL laminates may include similar facings, such as spunbond or other suitable nonwoven webs, with the facings in the NBL being neck-stretched. Furthermore, the facings in both the NBL and VFL processes may be adhesively or thermally bonded to an elastic core. The elastic core may be either a cast film for NBL or filament strands for VFL.

Figure 11:
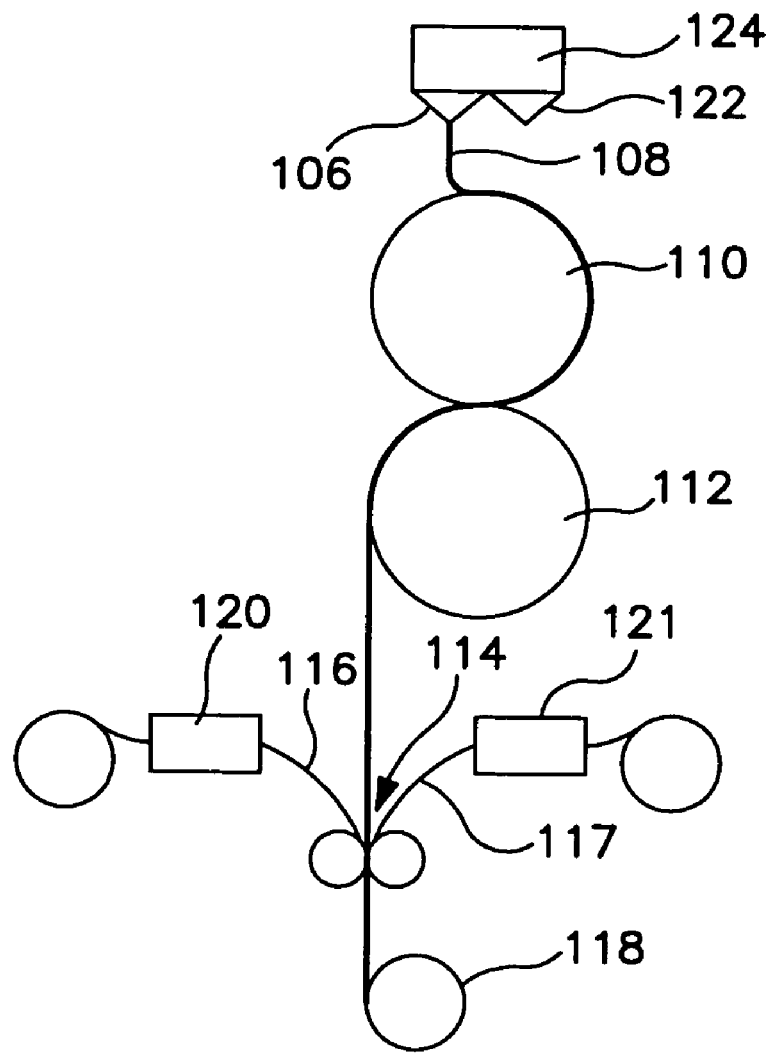
FIG. 11 is a schematic view of one embodiment of a combined NBL and VFL machine that may be used in the method of the invention.

The combination machine is based on a conventional VFL platfonm including a filament die 106 for extruding the elastic core 108 onto a first chill roll or forming roll 110, and a second roll 112 which passes the elastic core 108 to a nip 114 with the facings 116, 117 applied to the elastic core 108 prior to passing through the nip 114 and onto a winder 118. Additional equipment is added to the VFL platfonm to enable the production of NBL. The additional equipment includes ovens 120, 121 for neckstretching the facings 116, 117 and a film die 122 mounted adjacent the filament die 106. The similar throughputs of NBL and VFL, based on elastic basis weight and web width, enable the two processes to be combined into one machine while utilizing the same extruder 124 and pellet handling systems, or alternatively, conventional hot-melt equipment such as a melt tank or an extruder. One embodiment of the machine is illustrated in FIG. 11.

Figure 12:
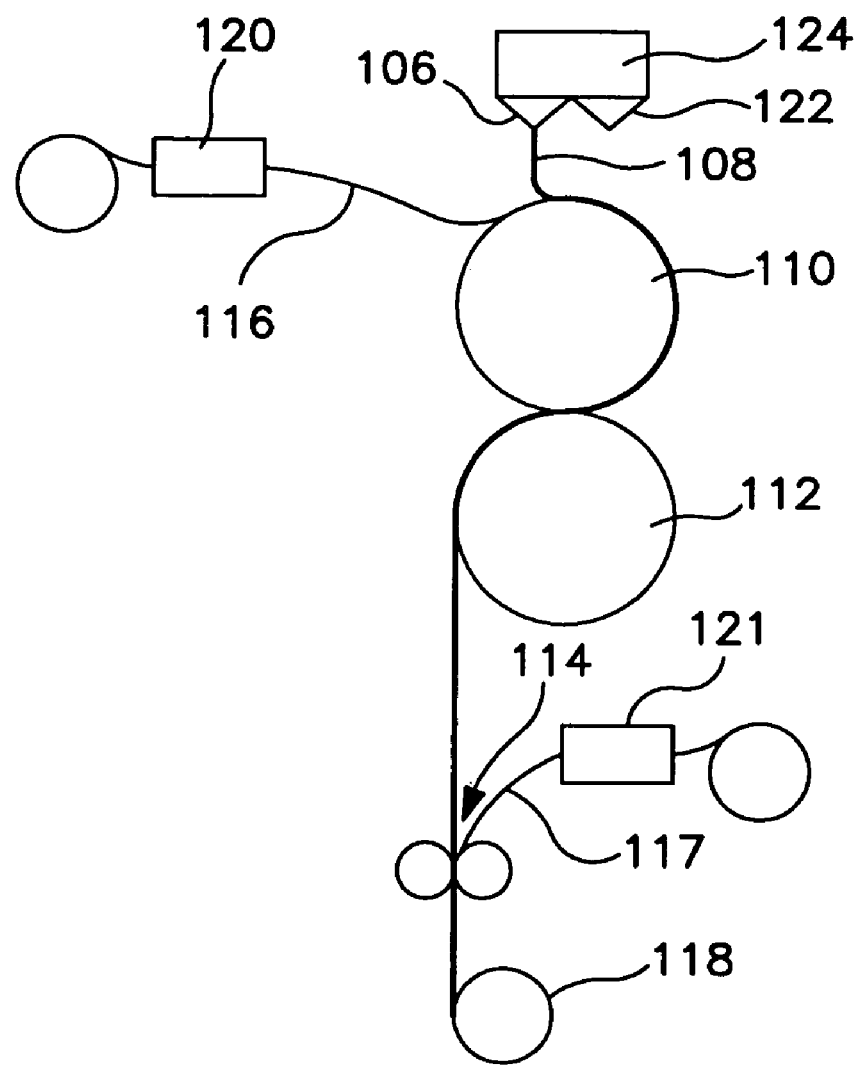
FIG. 12 is a schematic view of another embodiment of a combined NBL and VFL machine that may be used in the method of the invention.

Alternatively, the machine may be set up such that one of the facings 116 is guided onto the first forming roll 110 such that the elastic core 108 is extruded onto the facing 116. This embodiment of the machine is illustrated in FIG. 12.

Any of the elements of this machine can be combined with any of the elements of the preceding embodiments.

Test Methods

Adhesive Bond Strength

The adhesive bond strength of the elastomeric adhesive film of the present invention is determined as follows. A test sample of the elastic composite laminate having dimensions of about 2.0 inches (5.08 cm) wide by about 4.0 inches (10.16 cm) long, or as large as possible up to this size, is used for testing. The adhesive bond strength is determined through the use of a tensile tester, such as a SINTECH tensile tester commercially available from the Sintech Co., Carry, N.C., Model No. 11. A 90 degree peel adhesion test is run in order to determine the grams of force needed to pull apart the first and second layers of facing sheet of the laminate. Specifically, 1.25 inches (3.175 cm) or more of the 4-inch length of the test sample has the first and second layers of facing sheet peeled apart. The first facing sheet is then clamped in the upper jaw of the tensile tester, and the second facing sheet is clamped in the lower jaw of the tensile tester. The tensile tester is set to the following conditions:

Crosshead speed: 300 millimeters per minute
Full-scale load: 5,000 grams
Start measurements: 10 millimeters
Gauge length (jaw spacings): 1.0 inch (2.54 cm)

The Instron tensile tester is then engaged. The test is terminated after approximately 100 millimeters on a 2-inch by 2-inch sample. Twenty data points per second are collected for a total of about 400 data points. The average of these data points is reported as the adhesive bond strength. The results from the tensile tester are normalized to a sample having a width of 1 inch. At least three test samples are subjected to the above testing with the results being averaged and normalized to produce the reported adhesive bond strength.

Elongation

The elongation of an elastic composite laminate according to the present invention is suitably determined as follows. A 1-inch wide by 4-inch long sample of the laminate is provided. The central 3-inch (7.62 cm) area of the sample is marked. The test sample is then stretched to its maximum length, and the distance between the marks is measured and recorded as the "stretched to stop length." The percent elongation is determined according to the following formula:

{(stretched to stop length (in inches))−3}/3×100

If a 1-inch by 4-inch area is not available, the largest sample possible (but less than 1-inch by 4-inches) is used for testing with the method being adjusted accordingly.

Tension Force

The tension force of an elastic composite laminate according to the present invention is determined on a test sample of the laminate having a width of 1 inch (2.54 cm) and a length of 3 inches (7.62 cm). A test apparatus having a fixed clamp and an adjustable clamp is provided. The adjustable clamp is equipped with a strain gauge commercially available from S. A. Micier Co. under the trade designation Chatillon DFIS2 digital force gauge. The test apparatus can elongate the test sample to a given length. One longitudinal end of the test sample is clamped in the fixed clamp of the test apparatus with the opposite longitudinal end being clamped in the adjustable clamp fitted with the strain gauge. The test sample is elongated to 90 percent of its elongation (as determined by the test method set forth above). The tension force is read from the digital force gauge after 1 minute. At least three samples of the elasticized area are tested in this manner with the results being averaged and reported as grams force per inch width.

EXAMPLE

In this example, an elastomeric composite containing mutually reinforced elastomeric adhesive film and strand elements was prepared in accordance with the method of the invention. An elastomeric adhesive composition containing 40 wt % Dexco VECTOR 4111 SIS block polymer, 15 wt % Dexco VECTOR 4411 SIS block polymer, 45 wt %

ESCOREZ 5340 tackifier, and 0.5 wt % Ciba IRGANOX 1010 antioxidant was blended in a Sigma mixer. The elastic adhesive (Brookfield viscosity=47,000 cps @385 degrees Fahrenheit) was extruded from a melt tank as a film on a primary chill roll at 48 grams per square meter (gsm) before stretching. The melt tank temperature was in the range of 380-400 degrees Fahrenheit and the chill roll temperature was 11 degrees Celsius. The primary chill roll speed was 4 ft per min (fpm) and speeds for second, third, and nip rolls were respectively 7, 17, and 32 fpm.

The elastic strands were extruded onto the air side of the film on the second chill roll and immediately adhered on the film thereby forming a single unit composite. The strands were extruded at a spacing of 12 strands per inch from a filament die having orifice diameters of 0.030 inches. The strand output for the 12-inch wide die was 30 grams per minute (gpm). The strands were extruded from a twin screw extruder using a dryblend having the following composition: 90 wt % Dexco VECTOR 4111, 10 wt % Dexco ESCOREZ 5340. The melt temperature profile of the extruder was 120° C./175° C./190° C. and hose and die temperatures were respectively 200 degrees Celsius and 355 degrees Fahrenheit.

This composite containing the adhesive film and strands adhered to it was stretched as a unit (amounting to 8 times the initial length of the film) and then laminated between two layers of 0.5 osy Prism spunbond at a nip pressure of 95 psi. Neither the elastic film nor the strand showed breaks and the strands were self-aligned during the lamination process. The laminate made in this way appeared soft and gentle and exhibited high tension. The tension as measured shortly after production was 420 grams for a 2-inch wide sample which was stretched to 100% elongation from an initial length of 5 inches. No delamination was observed after aging at 130 degrees Fahrenheit for 1 week. The laminate also retained excellent elastic properties as evidenced by beneficially low and similar hysteresis loss factor values before and after aging, namely 19% before and 23% after aging, as well as high stretch-to-stop values in the range of 400%. Hysteresis loss factor was measured by the percentage difference between first cycle extension and second cycle retraction at 50% elongation.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. A method of making an elastomeric composite, comprising:
    casting a continuous non-foamed elastomeric adhesive film directly onto a first chill roll;
    separately extruding a plurality of continuous elastic strands directly onto the non-foamed film to create a continuous strand-reinforced composite; and
    stretching the continuous composite as a single unit.

2. The method of claim 1, further comprising passing the film onto a second chill roll and extruding the plurality of elastic strands onto the film while the film is in contact with the second chill roll.

3. The method of claim 1, comprising stretching the composite by at least 200%.

4. The method of claim 1, wherein the plurality of elastic strands comprises at least one of a group consisting of raw polymers, a mixture of polymers, and tackified polymers.

5. The method of claim 1, wherein the plurality of elastic strands comprises at least one of a group consisting of elastomeric polymer compositions, tackified polymers, olefinic copolymers, ethylene-propylene-diene monomer, styrene-isoprene-styrene, styrene-butadiene-styrene, styrene-ethylene/butylene-styrene, styrene-ethylene/propylene-styrene, polyurethane, polyisoprene, cross-linked polybutadiene, and combinations thereof.

6. The method of claim 1, wherein the plurality of elastic strands comprises a tackifier including at least one type of hydrocarbon selected from a group consisting of petroleum distillates, rosin, rosin esters, polyterpenes derived from wood, polyterpenes derived from synthetic chemicals, and combinations thereof.

7. The method of claim 1, wherein the elastomeric adhesive film comprises an elastomeric, hot melt, pressure-sensitive adhesive.

8. The method of claim 1, wherein the plurality of elastic strands comprises between about 5% and about 50% by weight of the composite.

9. The method of claim 1, wherein the plurality of elastic strands comprises between about 10% and about 35% by weight of the composite.

10. The method of claim 1, further comprising laminating the stretched composite between a first facing sheet and a second facing sheet.

11. The method of claim 10, wherein the first and second facing sheets are each selected from a group consisting of a nonwoven web and a film.

12. The method of claim 11, wherein the nonwoven web is selected from a spunbond web and a meltblown web.

13. The method of claim 1, wherein the plurality of elastic strands is extruded onto the elastomeric adhesive film at an add-on rate of between about 5 and about 50 grams per square meter before stretching.

14. The method of claim 13, further comprising controlling tension in the elastomeric composite through at least one of: selection of film composition, selection of strand composition, add-on rate, stretching the composite, selection of substrate, and combinations thereof.

15. A method of making an elastomeric composite, comprising:
    casting a continuous non-foamed elastomeric adhesive film directly onto a first chill roll;
    extruding a plurality of continuous elastic strands directly onto the non-foamed film to create a continuous strand-reinforced composite;
    stretching the continuous composite as a single unit; and
    laminating the stretched composite between a first facing sheet and a second facing sheet.

16. The method of claim 15, further comprising passing the film onto a second chill roll and extruding the plurality of elastic strands onto the film while the film is in contact with the second chill roll.

17. The method of claim 15, comprising casting the elastomeric adhesive film from a melt tank onto the first chill roll.

18. The method of claim 15, comprising casting the elastomeric adhesive film from a supply roll onto the first chill roll.

19. The method of claim 15, comprising extruding the plurality of elastic strands from a melt tank onto the film.

20. The method of claim 15, comprising extruding the plurality of elastic strands from an extruder onto the film.

21. The method of claim 15, comprising extruding the plurality of elastic strands from a supply roll onto the film.

22. A method of making an elastomeric composite laminate, comprising:

casting a continuous non-foamed elastomeric adhesive film directly onto a first chill roll;

passing the continuous non-foamed elastomeric adhesive film onto a second roll;

extruding a plurality of continuous elastic strands directly onto the non-foamed film while the film is on the second roll to create a continuous mutually-reinforced strand/film composite;

stretching the continuous composite as a single unit;

laminating the continuous stretched composite between a first facing sheet and a second facing sheet; and controlling tension in the elastomeric composite through at least one of: selection of film composition, selection of strand composition, add-on rate, stretching the composite, and combinations thereof.

* * * * *